(12) United States Patent
Inoue et al.

(10) Patent No.: US 6,406,830 B2
(45) Date of Patent: Jun. 18, 2002

(54) CHEMICAL AMPLIFICATION TYPE POSITIVE RESIST COMPOSITIONS AND SULFONIUM SALTS

(75) Inventors: Hiroki Inoue, Kashiba; Yasunori Uetani, Toyonaka, both of (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 09/849,523

(22) Filed: May 7, 2001

(30) Foreign Application Priority Data

May 9, 2000 (JP) ........................ 2000-135580
Aug. 25, 2000 (JP) ........................ 2000-255119

(51) Int. Cl.$^7$ ............................................. G03F 7/004
(52) U.S. Cl. .................... 430/270.1; 430/921; 430/922; 568/18; 568/77
(58) Field of Search ............................ 430/270.1, 921, 430/922; 568/18, 77

(56) References Cited

U.S. PATENT DOCUMENTS

| | | | |
|---|---|---|---|
| 3,616,314 A | * 10/1971 | Settineri | 204/59 |
| 4,028,110 A | * 6/1977 | Berendsen et al. | 96/66.3 |
| 4,056,634 A | * 11/1977 | Della-Bella et al. | 424/335 |
| 5,053,166 A | * 10/1991 | Murase et al. | 252/500 |
| 5,525,453 A | * 6/1996 | Przybilla et al. | 430/170 |
| 5,585,507 A | 12/1996 | Nakano et al. | |
| 5,587,488 A | * 12/1996 | Stenger-Smith et al. | 549/59 |
| 5,691,111 A | 11/1997 | Iwasa et al. | |
| 5,968,713 A | 10/1999 | Nozaki et al. | |
| 6,031,014 A | * 2/2000 | Crivello | 522/31 |
| 6,042,991 A | * 3/2000 | Aoal et al. | 430/285.1 |

FOREIGN PATENT DOCUMENTS

| EP | 789278 A2 | 8/1997 |
|---|---|---|
| EP | 982628 A2 | 3/2000 |
| JP | A-7-025846 | 1/1995 |
| JP | A-7-028237 | 1/1995 |
| JP | A-7-92675 | 4/1995 |
| JP | 792675 | 4/1995 |
| JP | A-8-027102 | 1/1996 |

OTHER PUBLICATIONS

Hofer et al., Journal of Photopolymer Science and Technology; vol. 9, No. 3, p. 387–398 (1996).
Takechi et al., Journal of Photopolymer Science and Technology, vol. 9, No. 3, p. 475–488 (1996).
Tolstikov et al., Izv. Akad. Nauk SSSR, Ser. Khim., vol. 8, p. 1924–1925, (1983), Abstract.
CA 100:5798 (1984:5798), G. A. Tolstikov et al., Stabilized sulfur bisylide–tetramethyl–1, 3–dislfuranylidene–2–propanone, Izv. Akad. Nauk SSSR, Ser. Khim. 1983, 8, 1924–5.*

* cited by examiner

Primary Examiner—Rosemary Ashton
(74) Attorney, Agent, or Firm—Birch, Stewart, Kolasch & Birch, LLP

(57) ABSTRACT

A chemical amplifying type positive resist composition having high transmittance, superior in sensitivity and resolution in a lithography utilizing a light having a wavelength of 220 nm or lower and confering a good profile is provided, Which comprises an aliphatic sulfonium salt represented by the following formula (I):

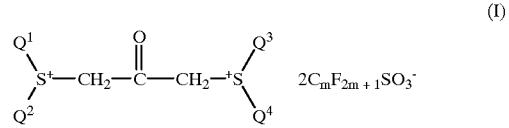

wherein either $Q^1$, $Q^2$, $Q^3$ and $Q^4$ represent an alkyl group or a cycloalkyl group, or $Q^1$ and $Q^2$ and/or $Q^3$ and $Q^4$ form, together with the adjacent sulfur atom, a heterocyclic group, and m represents an integer of 1 to 8;

at least one onium salt selected from the group consisting of a triphenylsulfonium salt and a diphenyliodonium salt; and a resin which contains a polymerization unit having a group unstable to an acid, and which is insoluble in alkali by itself but becomes soluble in alkali by the action of an acid.

12 Claims, No Drawings

CHEMICAL AMPLIFICATION TYPE POSITIVE RESIST COMPOSITIONS AND SULFONIUM SALTS

BACKGROUND OF THE INVENTION

The present invention relates to a chemical amplifying type positive resist composition used in the minute processing of a semiconductor and a novel compound usable as an acid generator in said resist composition.

In general, a lithography process using a resist composition has been adopted in the minute processing of a semiconductor. In lithography, the resolution can be improved with a decrease in wavelength of exposure light in principle as expressed by the equation of Rayleigh's diffraction limited. A g-line with a wavelength of 436 nm, an i-line with a wavelength of 365 nm, and a KrF excimer laser with a wavelength of 248 nm have been adopted as exposure light sources for lithography used in the manufacture of a semiconductor. Thus, the wavelength has become shorter year by year. An ArF excimer laser having a wavelength of 193 nm is considered to be promising as a next-generation exposure light source, and some of resists for ArF excimer laser are being made practical.

A lens used in an ArF excimer laser exposure machine or an exposure machine using a light-source of shorter wavelength has a shorter lifetime as compared with lenses for conventional exposure light sources. Accordingly, the shorter time required for exposure to ArF excimer laser light is desirable. For this reason, it is necessary to enhance the sensitivity of a resist. Consequently, there has been used a so-called chemical amplifying type resist, which utilizes the catalytic action of an acid generated due to exposure, and contains a resin having a group cleavable by the action of acid.

It is known that, desirably, resins used in a resist for ArF excimer laser exposure have no aromatic ring in order to ensure the transmittance of the resist, but have an alicyclic ring in place of an aromatic ring in order to impart a dry etching resistance thereto. Various kinds of resins such as those described in Journal of Photopolymer Science and Technology, Vol. 9, No. 3, pages 387–398 (1996) by D. C. Hofer, are heretofore known as such resins.

S. Takechi et al., Journal of Photopolymer Science and Technology, Vol. 9, No. 3, pages 475–487 (1996), and JP-A-9-73173 reported that, when a polymer or copolymer of 2-methyl-2-adamantyl methacrylate was used as the resin in a chemical amplifying type resist, 2-methyl-2-adamantyl was cleaved by the action of an acid to act as an positive type and a high dry etching resistance, a high resolution and a good adhesion to a substrate could be obtained. In addition, JP-A-10-274852 reported that the adhesion to a substrate was improved by using a resin having a butyrolactone residue in a part of polymerization units as the resin constituting a chemical amplification type positive resist composition. Further, JP-A-10-319595 described a resist composition containing a resin having a γ-butyrolactone-3-yl residue as a protective group for carboxyl group.

On the other hand, since the chemical amplification type resists utilizes the action of an acid, a problem arises that profiles are liable to be bottom-tailed by deactivation of the acid when the substrate is of a basic nature. It is known that this problem can be resolved by adding a much amount of a basic quencher substance. Addition of a much amount of such quencher substance, however, results in decrease of the sensitivity of the resist. In addition, in ArF-exposure, a resist is often applied on a substrate having a low reflection such as an organic or inorganic anti-reflective layer. When such a substrate having a low reflection is used, the profile of the resist generally deteriorated in a taper shape due to light absorption, although dimension uniformity is effectively improved.

One possible mean for lowering the light absorption is to reduce the amount of the acid generator. In this case, however, the sensitivity is generally decreased. Another mean for lowering the light absorption is to use an aliphatic sulfonium salt having a high transparency such as those described in JP-A-7-25846, JP-A-7-28237, JP-A-7-92675 and JP-A-8-27102. In the cases of these known aliphatic sulfonium salts, however, a sufficient resolution cannot be obtained and a problem that the profile on a basic substrate becomes bottom-tailed shape cannot be dissolved. Therefore, the chemical amplification type resists containing a conventional acid generator had a problem that performances, particularly the profile, are varied depending on the kind of the substrate.

An object of the present invention is to provide a chemical amplification type positive resist composition, which contains a resin component and an acid generator, which is suitable to use in excimer laser lithography with ArF, KrF or the like, particularly in lithography with a light having a wavelength of 220 nm or lower, for example, ArF excimer laser light, and which is superior in sensitivity and resolution confering a good profile.

Another object of the invention is to provide a compound useful as an acid generator in such a chemical amplification type positive resist composition.

The present inventors have found the fact that the transmittance and the resolution can be improved by using a combination of certain kinds of acid generators. Thus, the present invention has been completed.

SUMMARY OF THE INVENTION

The present invention provides a chemical amplifying type positive resist composition comprising an aliphatic sulfonium salt represented by the following formula (I):

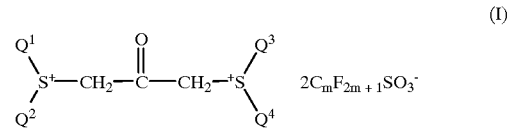

wherein either $Q^1$, $Q^2$, $Q^3$ and $Q^4$ independently represent an alkyl group having 1 to 6 carbon atoms or a cycloalkyl group having 3 to 10 carbon atoms, or $Q^1$ and $Q^2$ and/or $Q^3$ and $Q^4$ independently form, together with the adjacent sulfur atom, a heterocyclic group which has 2 to 8 carbon atoms and which may further have an oxygen atom or a sulfur atom, and m represents an integer of 1 to 8;

at least one onium salt selected from the group consisting of a triphenylsulfonium salt represented by the following formula (IIa) and a diphenyliodonium salt represented by the following formula (IIb):

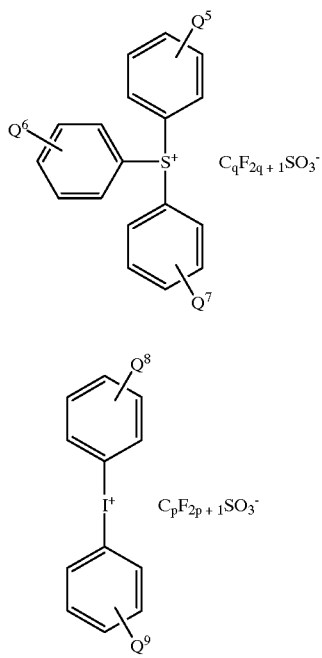

(IIa)

(IIb)

wherein $Q^5$, $Q^6$, $Q^7$, $Q^8$ and $Q^9$ independently represent a hydrogen atom, a hydroxyl group, an alkyl group having 1 to 6 carbon atoms or an alkoxy group having 1 to 6 carbon atoms, and p and q represent integer of 1 to 8; and a resin which contains a polymerization unit having a group unstable to an acid, and which is insoluble in alkali by itself but becomes soluble in alkali by the action of an acid.

The aliphatic sulfonium salt represented by the above formula (I) is a novel compound never described in literature. Therefore, the invention also provides the sulfonium compound represented by the above formula (I).

DETAILED DESCRIPTION OF THE INVENTION

The acid generator used in the chemical amplification type resist composition is a substance that decomposes to generate an acid by acting a radiation such as a light or an electronic ray on the substance itself or a resist composition containing the substance. In the resist composition of the invention, both of an aliphatic sulfonium salt represented by the above formula (I), and at least one onium salt selected from the group consisting of a triphenylsulfonium salt represented by the above formula (IIa) and a diphenyliodonium salt represented by the above formula (IIb). Such acid generators are used together.

In the formula (I), either $Q^1$, $Q^2$, $Q^3$ and $Q^4$ independently represent an alkyl group having 1 to 6 carbon atoms or a cycloalkyl group having 3 to 10 carbon atoms. Alternatively, $Q^1$, $Q^2$ and the sulfur atom bonding to them, and/or $Q^3$, $Q^4$ and the sulfur atom bonding to them may form a heterocyclic group which has 2 to 8 carbon atoms and which may further have an oxygen atom or a sulfur atom. When the alkyl group has 3 or more carbon atoms, the group can be straight-chained or branched. Typical examples of the alkyl group include methyl, ethyl, propyl, isopropyl, butyl, tert-butyl, pentyl, hexyl and the like. Typical examples of the cycloalkyl group include cyclopentyl, cyclohexyl, cycloheptyl and the like. Typical examples of the heterocyclic groups formed by $Q^1$, $Q^2$ and the sulfur atom bonding to them, and those formed by $Q^3$, $Q^4$ and the sulfur atom bonding to them include ethylene sulfide, trimethylene sulfide, tetrahydrothiophene, tetrahydrothiopyran, thioxane, dithian, tetrahydrothiophene-3-one, tetrahydrothiopyran-4-one and the like. In the formula (I), m representing the number of carbon atoms in an alkane moiety constituting a perfluoroalkanesulfonate anion is an integer of 1 to 8. Typical examples of the moiety corresponding to the perfluoroalkanesulfonate anion include trifluoromethanesulfonate ion, perfluorobutanesulfonate ion, perfluorooctanesulfonate ion and the like.

The aliphatic sulfonium salt represented by the formula (I) has a high transmittance with respect to a light having a wavelength of 220 nm, such as ArF excimer laser light having a wavelength of 193 nm, since the groups constituting the sulfonium cation is non-aromatic groups. Therefore, when such an aliphatic sulfonium salt is used as an acid generator, a resist composition containing the acid generator has a smaller rate of absorption for a short wavelength exposure light as described above, and can avoid a bottom-tailed profile.

The aliphatic sulfonium compound represented by the formula (I) can be produced according to the known method. For example, they can be produced according to the following scheme by applying a method described by J. V. Crivello et al., Journal of Polymer Science, Polymer Chemistry Edition, Vol. 17, 2877–2892 (1979):

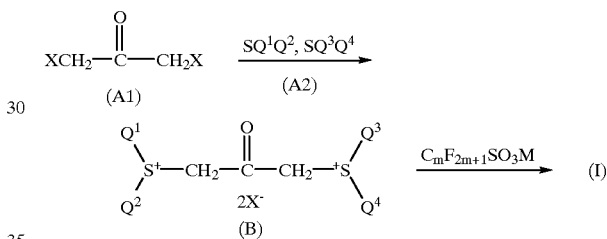

wherein $Q^1$, $Q^2$, $Q^3$, $Q^4$ and m are as defined above, X represents a halogen such as bromine and iodine, and M represents an alkali metal such as sodium and potassium or silver.

An aliphatic sulfonium salt represented by the formula (I) can be obtained by acting a sulfide compound of the formula (A2) on a dihalogenoacetone of the formula (A1) to give a sulfonium halide of the formula (B), followed by further acting a metal salt of a perfluoroalkanesulfonic acid of the formula: $C_mF_{2m+1}SO_3M$. These reactions are carried out in an appropriate solvent, such as acetone, acetonitrile, nitromethane or the like. The sulfide compound of the formula (A2) is used in an amount preferably of 1.8 to 3 moles, more preferably of 2.0 to 2.2 moles, based on 1 mole of the dihalogenoacetone corresponding to the formula (A1). The metal salt of a perfluoroalkanesulfonic acid of the formula: $C_mF_{2m+1}SO_3M$ may be used preferably in an amount of 0.8 to 1.2 mole, more preferably 0.9 to 1.1 mole, based on 1 mole of the sulfide compound of the formula (A2) used for the production of the sulfonium halide of the formula (B). After completion of the reaction, the aliphatic sulfonium salt can be obtained by removing the generated metal halide salt by filtration or the like and subjecting the solution to a post-treatment such as concentration, recrystallization or others.

Specific examples of the aliphatic sulfonium salt represented by the formula (I) include the following compounds:

(2-oxo-1,3-propanediyl)bis(dimethylsulfonium) bis (trifluoromethanesulfonate),
(2-oxo-1,3-propanediyl)bis(dimethylsulfonium) bis (perfluorobutanesulfonate), (2-oxo-1,3-propanediyl)bis(dimethylsulfonium) bis(perfluorooctanesulfonate),
(2-oxo-1,3-propanediyl)bis(diethylsulfonium) bis(perfluorobutanesulfonate),
(2-oxo-1,3-propanediyl)bis(dibutylsulfonium) bis(trifluoromethanesulfonate),
(2-oxo-1,3-propanediyl)bis(dibutylsulfonium) bis(perfluorobutanesulfonate),
(2-oxo-1,3-propanediyl)bis(dibutylsulfonium) bis(perfluorooctanesulfonate),
(2-oxo-1,3-propanediyl)bis(diisopropylsulfonium) bis(perfluorobutanesulfonate),
(2-oxo-1,3-propanediyl)bis(tert-butylmethylsulfonium) bis(perfluorobutanesulfonate),
(2-oxo-1,3-propanediyl)bis(cyclohexylmethylsulfonium) bis(perfluorobutanesulfonate),
1,1'-(2-oxo-1,3-propanediyl)bis(tetrahydrothiophenium) bis(trifluoromethanesulfonate),
1,1'-(2-oxo-1,3-propanediyl)bis(tetrahydrothiophenium) bis(perfluorobutanesulfonate),
1,1'-(2-oxo-1,3-propanediyl)bis(tetrahydrothiophenium) bis(perfluorooctanesulfonate),
1,1'-(2-oxo-1,3-propanediyl)bis(tetrahydrothiopyranium) bis(perfluorobutanesulfonate),
1,1'-(2-oxo-1,3-propanediyl)bis(1,4-thioxolanium) bis(perfluorobutanesulfonate),
1,1'-(2-oxo-1,3-propanediyl)bis(4-oxotetrahydrothiopyranium) bis(perfluorobutanesulfonate) and the like.

In the present invention, at least one onium salt selected from the group consisting of compounds of the formula (IIa) and the formula (IIb) is used as the acid generator together with the aliphatic sulfonium salt of the formula (I). In these onium salts, $Q^5$, $Q^6$, $Q^7$, $Q^8$ and $Q^9$ respectively represent a hydrogen atom, a hydroxyl group, an alkyl group having 1 to 6 carbon atoms or an alkoxy group having 1 to 6 carbon atoms. When the alkyl group or the alkoxy group has 3 or more carbon atoms, such group can be straight-chained or branched. Typical examples of the alkyl group include methyl, ethyl, propyl, isopropyl, butyl, tert-butyl, pentyl, hexyl and the like. Typical examples of the alkoxy group include methoxy, ethoxy, propoxy, butoxy and the like. In the formulae (IIa) and (IIb), p and q representing the numbers of carbon atoms in alkane moieties constituting perfluoroalkanesulfonate anion are integers of 1 to 8.

The triphenylsulfonium salt represented by the formula (IIa) and the diphenyliodonium salt represented by the formula (IIb) can be commercial products thereof, if available. Otherwise, they can be produced according to the conventional process. As to the process for producing the triphenylsulfonium salt (IIa), following processes can be exemplified: a process in which the corresponding triphenylsulfoniumbromide is reacted with a silver perfluoroalkanesulfonate, a process in which the corresponding diphenylsulfoxide is reacted with a benzene compound and a perfluoroalkanesulfonic acid in the presence of trifluoroacetic anhydride according to the description in Chemical and Pharmaceutical Bulletin, Vol. 29, 3753 (1981), a process in which a corresponding aryl Grignard reagent is reacted with thionyl chloride, then with a triorganosilyl halide to give a triarylsulfonium halide, followed by a reaction with a silver perfluoroalkanesulfonate according to the description in JP-A-8-311018, and so on. Compounds of the formula (IIa) wherein at least one of $Q^5$, $Q^6$ and $Q^7$ is hydroxyl group can be produced by treating a triphenylsulfonium salt having a tert-butoxy group on the benzene ring with a sulfonic acid having the same anion as that of the triphenylsulfonium salt to eliminate the tert-butyl group according to the description in the same JP-A-8-311018.

As to the process for producing the diphenyliodonium salt (IIb), following processes can be exemplified: a process in which iodyl sulfate is reacted with a corresponding aryl compound, followed by addition of a perfluoroalkanesulfonic acid according to the description in Journal of American Chemical Society, Vol. 81, 342 (1959), a process in which concentrated sulfuric acid is added dropwise to a mixture of a corresponding aryl compound, acetic anhydride and potassium iodate to cause a reaction, followed by addition of a perfluoroalkanesulfonic acid, a process in which a reaction product obtained by adding iodine and trifluoroacetic acid to a mixed solution of acetic anhydride and fuming nitric acid is reacted with a corresponding aryl compound, followed by addition of a perfluoroalkanesulfonic acid, and so on.

Specific examples of the triphenylsulfonium salt corresponding to the formula (IIa) and the diphenyliodonium salt corresponding to the formula (IIb) include the following compounds:

triphenylsulfonium trifluoromethanesulfonate,
triphenylsulfonium perfluorobutanesulfonate,
triphenylsulfonium perfluorooctanesulfonate,
4-methylphenyldiphenylsulfonium trifluoromethanesulfonate,
4-methylphenyldiphenylsulfonium perfluorobutanesulfonate,
4-hydroxyphenyldiphenylsulfonium perfluorobutanesulfonate,
4-methoxyphenyldiphenylsulfonium perfluorobutanesulfonate,
tris(4-methylphenyl)sulfonium perfluorobutanesulfonate,
tris(4-methoxyphenyl)sulfonium perfluorobutanesulfonate,
triphenylsulfonium perfluorooctanesulfonate,
4-methylphenyldiphenylsulfonium perfluorooctanesulfonate,
4-hydroxyphenyldiphenylsulfonium perfluorooctanesulfonate,
4-methoxyphenyldiphenylsulfonium perfluorooctanesulfonate,
tris(4-methylphenyl)sulfonium perfluorooctanesulfonate,
tris(4-methoxyphenyl)sulfonium perfluorooctanesulfonate,
diphenyliodonium perfluorobutanesulfonate,
di(4-methoxyphenyl)iodonium perfluorooctanesulfonate,
di(4-tert-butylphenyl)iodonium perfluorooctanesulfonate, and the like.

The resin component constituting the resist composition of the invention contains a polymerization unit having a group unstable to an acid. The resin for use in a chemical amplifying type positive resist is generally alkali-insoluble or hardly alkali-soluble by itself. However, a part of a group therein is cleaved by the action of an acid, and the resin becomes alkali-soluble after the cleavage. The group unstable to an acid in the invention can be various groups conventionally known in the art. Examples of the group unstable to an acid include various esters of carboxylic acid. Examples of the esters of carboxylic acid include alkyl esters such as methyl ester and tert-butyl ester, acetal type esters such as methoxymethyl ester, ethoxymethyl ester, 1-ethoxyethyl ester, 1-isobutoxyethyl ester, 1-isopropoxyethyl ester, 1-ethoxypropyl ester, 1-(2-methoxyethoxy)ethyl ester, 1-(2-acetoxyethoxy)ethyl ester, 1-[2-(1-adamantyloxy)ethoxy]ethyl ester, 1-[2-(1-adamantanecarbonyloxy)ethoxy]ethyl ester, tetrahydro-2-furyl ester and tetrahydro-2-pyranyl ester, alicyclic esters such as isobornyl ester and 2-alkyl-2-adamantyl ester, and the like. Examples of the monomers leading these polymerization units having a carboxylic ester include (meth)acrylic monomer such as methacrylic ester and acrylic ester, and alicyclic monomers having a carboxylic ester bound thereto such as norbornenecarboxylic ester, tricyclodecenecarboxylic ester and tetracyclodecenecarboxylic ester.

Among the polymerization unit having a group unstable to an acid, a polymerization unit of 2-alkyl-2-adamantyl (meth)acrylate is preferable from a viewpoint of resolution of the resist containing it. This polymerization unit can be formed by opening the double bond of (meth)acrylic acid moiety in the 2-alkyl-2-adamantyl acrylate or 2-alkyl-2-adamantyl methacrylate, and is specifically represented by the following formula (III):

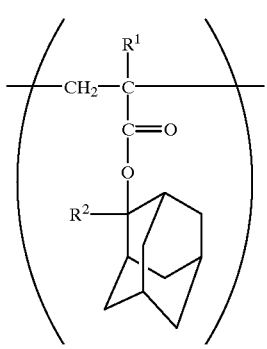

(III)

wherein $R^1$ represents hydrogen or methyl and $R^2$ represents alkyl,

The polymerization unit of 2-alkyl-2-adamantyl (meth)acrylate represented by the formula (III) ensures the transmittance of a resist and contributes to the improvement of dry etching resistance due to the presence of an adamantane ring. Further, the 2-alkyl-2-adamantyl in this unit is cleaved by the action of an acid. Hence, this unit contributes to the enhancement of alkali-solubility after exposure to radiation of a resist film. $R^2$ in the formula (I) is alkyl. This alkyl may have, for example, about 1 to 8 carbon atoms. In general, the alkyl is advantageously straight-chained, but it may be branched when the number of carbons is 3 or more. Specific examples of $R^2$ include methyl, ethyl, propyl, isopropyl, butyl and the like. Among them, those having methyl or ethyl as $R^2$ are preferred for the improvement of adhesion between the resist film and the substrate and for the improvement of resolution.

Specific examples of monomers leading the polymerization unit of 2-alkyl-2-adamantyl (meth)acrylate represented by the formula (III) include 2-methyl-2-adamantyl acrylate, 2-ethyl-2-adamantyl acrylate, 2-methyl-2-adamantyl methacrylate, 2-ethyl-2-adamantyl methacrylate and the like. The 2-alkyl-2-adamantyl (meth)acrylate can generally be produced by the reaction of a 2-alkyl-2-adamantanol or a metal salt thereof with an acrylic halide or methacrylic halide.

The resin defined in the invention can also contain another polymerization unit that is not cleaved or is hardly cleaved by the action of an acid in addition to a polymerization unit having a group unstable to an acid as described above. Examples of another possible polymerization unit include those derived from monomers having a free carboxylic acid group such as acrylic acid or methacrylic acid, those derived from aliphatic unsaturated dicarboxylic anhydride such as maleic anhydride or itaconic anhydride, those derived from 2-norbornene, those derived from (meth)acrylonitrile, those derived from various (meth)acrylic esters such as 2-hydroxyethyl (meth)acrylate, 3-hydroxy-1-adamantyl (meth)acrylate, (meth)acryloyloxy-γ-butyrolactone, and the like.

Particularly, the polymerization units of 3-hydroxy-1-adamantyl (meth)acrylate and polymerization units of (meth)acryloyloxy-γ-butyrolactone in which the lactone ring is unsubstituted or substituted with an alkyl are preferred from the viewpoint of adhesiveness of the resist film to the substrate. The polymerization unit of 3-hydroxy-1-adamantyl (meth)acrylate cited herein means a unit formed by opening the double bond of the (meth)acrylic acid moiety in the corresponding 3-hydroxy-1-adamantyl(meth)acrylate. The polymerization unit of (meth)acryloyloxy-γ-butyrolactone in which the lactone ring is unsubstituted or substituted with an alkyl herein means a unit formed by opening the double bond of the (meth)acrylic acid moiety in α-(meth)acryloyloxy-γ-butyrolactone which is unsubstituted or alkyl-substituted in the lactone ring, or a unit formed by opening the double bond of the (meth)acrylic acid moiety in β-(meth)acryloyloxy-γ-butyrolactone which is unsubstituted or alkyl-substituted in the lactone ring.

The polymerization units derived from 3-hydroxy-1-adamantyl(meth)acrylate, α-(meth)acryloyloxy-γ-butyrolactone which is unsubstituted or alkyl-substituted in the lactone ring, and β-(meth)acryloyloxy-γ-butyrolactone which is unsubstituted or alkyl-substituted in the lactone ring can be represented, respectively, by the following formulae (IV), (V) and (VI):

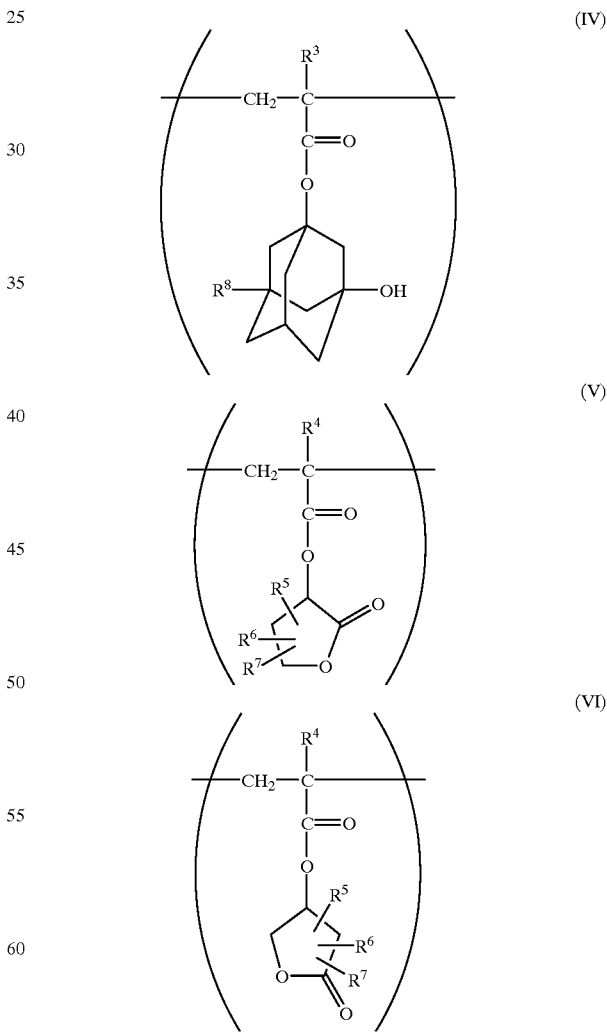

wherein $R^3$ and $R^4$ independently represent hydrogen or methyl, $R^5$, $R^6$ and $R^7$ independently represent hydrogen or alkyl and $R^8$ represents hydrogen or hydroxyl.

The 3-hydroxy-1-adamantyl (meth)acrylate for leading a unit of the formula (IV) is commercially available and can be produced, for example, by reacting the corresponding hydroxyadamantane with (meth)acrylic acid or a halide thereof. The α- or β-(meth)acryloyloxy-γ-butyrolactone for leading a unit of the formula (V) or (VI) can be produced by reacting acrylic acid or methacrylic acid with α- or β-bromo-γ-butyrolactone in which the lactone ring is unsubstituted or substituted with an alkyl, or by reacting an acrylic halide or methacrylic halide with α- or β-hydroxy-γ-butyrolactone in which the lactone ring is unsubstituted or substituted with an alkyl.

All the polymerization unit of 3-hydroxy-1-adamantyl (meth)acrylate represented by the formula (IV), the polymerization unit of α-(meth)acryloyloxy-γ-butyrolactone represented by the formula (V) and the polymerization unit of β(meth)acryloyloxy-γ-butyrolactone represented by the formula (VI) have a high polarity and confer an improved adhesiveness between the resist film containing any of them to the substrate. In addition, these polymerization units also contribute to the improvement of the resolution of the resist. Furthermore, the polymerization unit of 3-hydroxy-1-adamantyl (meth)acrylate contributes to the improvement of the dry etching resistance of a resist. Moreover, the polymerization unit of β-methacryloyloxy-γ-butyrolactone contributes to the improvement of transmittance of the resist.

Examples of the monomers for leading the polymerization unit of 3-hydroxy-1-adamantyl (meth)acrylate represented by the formula (IV) include 3-hydroxy-1-adamantyl acrylate, 3-hydroxy-1-adamantyl methacrylate, 3,5-dihydroxy-1-adamantyl acrylate, 3,5-dihydroxy-1-adamantyl methacrylate and so on. In the formula (V) and the formula (VI), $R^5$, $R^6$ and $R^7$ are respectively hydrogen or alkyl. This alkyl may have about 1 to 6 carbon atoms and when the alkyl group has 3 or more carbon atoms, the group can be straight-chained or branched. Typical examples of the alkyl represented by $R^5$, $R^6$ and $R^7$ include methyl, ethyl, propyl, butyl and the like. Examples of monomers for leading the polymerization unit of α-(meth)acryloyloxy-γ-butyrolactone represented by the formula (V) include α-acryloyloxy-γ-butyrolactone,
α-methacryloyloxy-γ-butyrolactone,
α-acryloyloxy-β,β-dimethyl-γ-butyrolactone,
α-methacryloyloxy-β,β-dimethyl-γ-butyrolactone,
α-acryloyloxy-α-methyl-γ-butyrolactone,
α-methacryloyloxy-α-methyl-γ-butyrolactone and the like.

Examples of monomers leading the polymerization unit of

β-(meth)acryloyloxy-γ-butyrolactone represented by the formula (VI) include β-acryloyloxy-γ-butyrolactone,
β-methacryloyloxy-γ-butyrolactone,
β-methacryloyloxy-α-methyl-γ-butyrolactone and the like.

Resins containing a polymerization unit of 2-norbornene have a strong structure, because they have an alicyclic ring directly in the main chain. As the result, they are excellent in dry etching resistance. The polymerization unit of 2-norbornene can be introduced, for example, by a radical polymerization using an aliphatic unsaturated dicarboxylic anhydride such as maleic anhydride or itaconic anhydride together with the corresponding 2-norbornene. Therefore, the polymerization unit of 2-norbornene is a unit formed by opening the double bond therein and can be represented by the formula (VII). The polymerization units of maleic anhydride and the polymerization unit of itaconic anhydride as the polymerization units of the aliphatic unsaturated dicarboxylic anhydrides are units formed by opening the double bonds therein and can be represented by the formulae (VIII) and (IX).

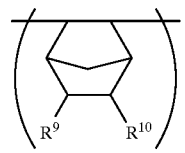

(VII)

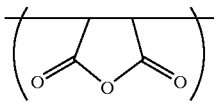

(VIII)

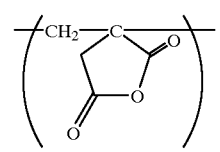

(IX)

In the formula (VII), either $R^9$ and $R^{10}$ independently represent hydrogen, alkyl having 1 to 3 carbon atoms, hydroxyalkyl having 1 to 3 carbon atoms, carboxyl, cyano or the group: —COOZ wherein Z is an alcohol residue, or $R^9$ and $R^{10}$ may be combined together to form a carboxylic anhydride residue represented by —C(=O)OC(=O)—. Specific examples of alkyl represented by $R^9$ or $R^{10}$ include methyl, ethyl, propyl and the like. Specific examples of hydroxyalkyl represented by $R^9$ or $R^{10}$ include hydroxymethyl, 2-hydroxyethyl and the like. Examples of the alcohol residue represented by Z include alkyl with about 1 to 8 carbon atoms, which is unsubstituted or substituted, 2-oxooxolane-3- or -4-yl and the like. Possible substituents on the alkyl include a hydroxyl group, an alicyclic hydrocarbon residue and the like. Specific examples of carboxylic ester group represented by —COOZ include methoxycarbonyl, ethoxycarbonyl,
  2-hydroxyethoxycarbonyl,
tert-butoxycarbonyl, 2-oxooxolane-3-yloxycarbonyl,
2-oxooxolane-4-yloxycarbonyl,
1,1,2-trimethylpropoxycarbonyl,
1-cyclohexyl-1-methylethoxycarbonyl,
1-(4-methylcyclohexyl)-1-methylethoxycarbonyl,
1-(1-adamantyl)-1-methylethoxycarbonyl and the like.

Examples of monomers for leading the polymerization unit of formula (VII) include 2-norbornene, 2-hydroxy-5-norbornene,
5-norbornene-2-carboxylic acid, methyl
5-norbornene-2-carboxylate, t-butyl
5-norbornene-2-carboxylate, 1-cyclohexyl-1-methylethyl
5-norbornene-2-carboxylate,
1-(4-methylcyclohexyl)-1-methylethyl
5-norbornene-2-carboxylate,
1-(4-hydroxylcyclohexyl)-1-methylethyl
5-norbornene-2-carboxylate,
1-methyl-1-(4-oxocyclohexyl)ethyl
5-norbornene-2-carboxylate,
1-(1-adamantyl)-1-methylethyl 5-norbornene-2-carboxylate,
1-methylcyclohexyl 5-norbornene-2-carboxylate, 2-methyl-2-adamantyl 5-norbornene-2-carboxylate,
2-ethyl-2-adamantyl 5-norbornene-2-carboxylate,
2-hydroxyl-1-ethyl 5-norbornene-2-carboxylate,
5-norbornene-2-methanol
5-norbornene-2,3-dicarboxylic acid anhydride, and the like.

Depending on the kind of radiation for patterning exposure and the kind of group unstable to an acid, it is generally preferred that the resin used in the invention contains the polymerization unit having a group unstable to an acid in a range of 10 to 80% by mole based on the total resin. Particularly, when the polymerization unit of 2-alkyl-2-adamantyl (meth)acrylate represented by the formula (III) is used as the group unstable to an acid, it is preferred that the unit exists in 15% by mole or more based on the total resin. When, in addition to the polymerization unit having a group unstable to an acid, another polymerization unit hardly cleavable by the action of an acid, such as the polymerization unit of 3-hydroxy-1-adamantyl (meth)acrylate represented by the formula (IV), the polymerization unit of α-(meth)acryloyloxy-γ-butyrolactone represented by the formula (V), the polymerization unit of β-(meth)acryloyloxy-γ-butyrolactone represented by the formula (VI), the polymerization unit of 2-norbornene represented by the formula (VII), the polymerization unit of maleic anhydride represented by the formula (VIII) and the polymerization unit of itaconic anhydride represented by the formula (IX) as the polymerization units of the aliphatic unsaturated dicarboxylic anhydrides, are present, it is preferred that these units exist within a range of 20 to 90% by mole in total based on the total resin.

When a copolymer containing the polymerization unit of 3-hydroxy-1-adamantyl (meth)acrylate represented by the formula (IV) and/or the polymerization unit of α-(meth)acryloyloxy-γ-butyrolactone represented by the formula (V) as well as the polymerization unit of 2-norbornene represented by the formula (VII) and the polymerization unit of the aliphatic unsaturated dicarboxylic anhydrides represented by the formula (VIII) or (IX) together with the polymerization unit having a group unstable to an acid containing a unit of 2-alkyl-2-adamantyl (meth)acrylate represented by the formula (III) is desired, it is usual to copolymerize a monomer mixture containing 10 to 80% by mole of a monomer having a group unstable to an acid, particularly 15% by mole or more of 2-alkyl-2-adamantyl (meth)acrylate for leading a unit of the formula (III), and 20 to 90% by mole in total of 3-hydroxy-1-adamantyl (meth)acrylate for leading the unit of the formula (IV) and/or α-(meth)acryloyloxy-γ-butyrolactone for leading the unit of the formula (V) as well as a 2-norbornene compound for leading the unit of the formula (VII) and a monomer for leading the polymerization unit of aliphatic unsaturated dicarboxylic anhydride for leading the unit of the formula (VIII) or (IX). When a 2-norbornene compound and an aliphatic unsaturated dicarboxylic anhydride are used as monomers for copolymerization, it is preferred to use them in excess in view of the fact that these have a tendency of hardly polymerizing. Likewise, when a copolymer containing a polymerization unit of β-(meth)acryloyloxy-γ-butyrolactone represented by the formula (VI) together with a polymerization unit having a group unstable to an acid is desired, it is advantageous to polymerize a monomer mixture containing 10 to 80% by mole of a monomer having a group unstable to an acid and 20 to 90% by mole of β-(meth)acryloyloxy-γ-butyrolactone for leading the unit of the formula (VI).

It is also known that, generally in a chemical amplifying type positive resist composition, performance deterioration due to the deactivation of an acid associated with leaving after exposure can be reduced by adding a basic compound, especially a basic nitrogen-containing organic compound such as amines as a quencher. It is also preferable in the present invention that such basic compounds are added. Concrete examples of the basic compounds to be used as quenchers include the ones represented by the following formulae:

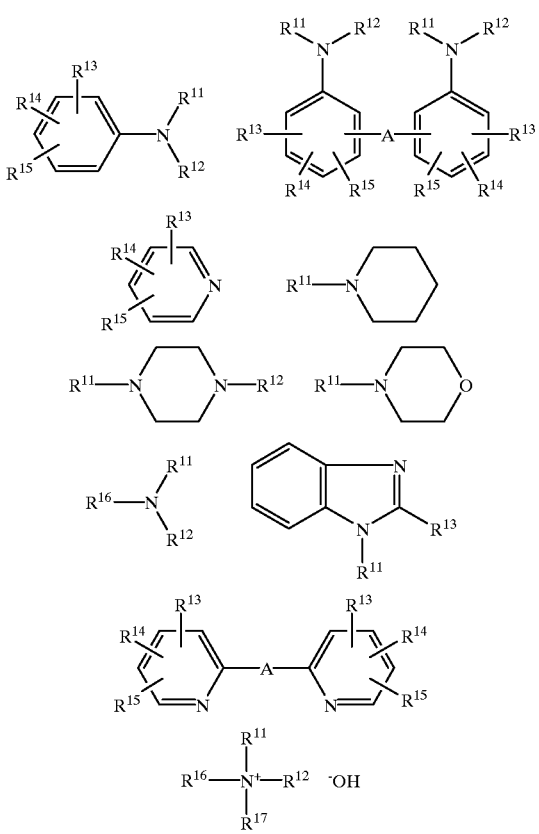

wherein $R^{11}$, $R^{12}$ and $R^{17}$ represent, independently each other, hydrogen, cycloalkyl, aryl or alkyl which may be optionally substituted with a hydroxyl, amino which may be optionally substitiuted with alkyl having 1 to 6 carbon atoms, or alkoxy having 1 to 6 carbon atoms; $R^{13}$, $R^{14}$ and $R^{15}$, which are same or different from each other, represent hydrogen, cycloalkyl, aryl, alkoxy or alkyl which may be optionally substituted with a hydroxyl, amino which may be optionally substitiuted with alkyl having 1 to 6 carbon atoms, or alkoxy having 1 to 6 carbon atoms; $R^{16}$ represents cycloalkyl or alkyl which may be optionally substituted with a hydroxyl, amino which may be optionally substitiuted with alkyl having 1 to 6 carbon atoms, or alkoxy having 1 to 6 carbon atoms; A represents alkylene, carbonyl, imino, sulfide or disulfide. The alkyl represented by $R^{11}$ to $R^{17}$ and alkoxy represented by $R^{13}$ to $R^{15}$ may have about 1 to 6 carbon atoms. The cycloalkyl represented by $R^{11}$ to $R^{17}$ may have about 5 to 10 carbon atoms and the aryl represented by $R^{11}$ to $R^{15}$ and $R^{17}$ may have about 6 to 10 carbon atoms. The alkylene represented by A may have about 1 to 6 carbon atoms and may be straight-chained or branched.

Among the basic compounds as described above, 2,6-dialkylpyridine compound represented by the formula (X) is preferable for improving the storage stability of the resist:

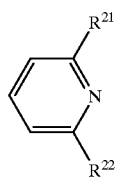

(X)

wherein $R^{21}$ and $R^{22}$ independently represent an alkyl having 1–4 carbon atoms. Concrete examples of the 2,6-dialkylpyridine compound include 2,6-lutidine, 2-ethyl-6-methylpyridine, 2,6-di-tert-butylpyridine, and the like. The 2,6-dialkylpyridine compound can be used alone or together with other basic compounds as a quencher.

The resist composition of the present invention preferably contains the resin in an amount in the range of 80 to 99.9% by weight, and the acid generator in an of 0.1 to 20% by weight based on the total amount of the resin and the acid generator.

In the resist composition of the present invention, the ratio by weight of the aliphatic sulfonium salt of the formula (I) to the onium salt selected from the group consisting of a triphenylsulfonium salt of the formula (IIa) and a diphenyliodonium salt of the formula (IIb) is preferably about 9:1 to 1:9, more preferably about 8:2 to 2:8.

When a basic compound is used as a quencher, it is preferably contained in an amount in the range of 0.0001 to 0.1% by weight based on the total solid component weight of the resist composition. The composition may also contain, if required, various additives such as sensitizers, dissolution inhibitors, resins other than resin, surfactants, stabilizers, and dyes so far as the objects of the present invention is not harmed.

The resist composition of the present invention generally becomes a resist solution in the state in which the above-described components are dissolved in a solvent to be applied on a substrate such as a silicon wafer. The solvent herein used may be one which dissolves each component, has an appropriate drying rate, and provides a uniform and smooth coating after evaporation of the solvent, and can be one which is generally used in this field. Examples thereof include glycol ether esters such as ethylcellosolve acetate, methylcellosolve acetate, and propylene glycol monomethyl ether acetate; esters such as ethyl lactate, butyl acetate, amyl acetate, and ethyl pyruvate; ketones such as acetone, methyl isobutyl ketone, 2-heptanone, and cyclohexanone; and cyclic esters such as γ-butyrolactone. These solvents can be used alone or in combination of two or more thereof.

The resist film applied on a substrate, and dried is subjected to an exposure treatment for patterning. Then, after a heat-treatment for promoting a protecting deblocking reaction, development by an alkali developer is conducted. The alkali developer herein used can be various kinds of alkaline aqueous solutions used in this field. In general, an aqueous solution of tetramethylammoniumhydroxide or (2-hydroxyethyl)trimethylammoniumhydroxide (so-called colline) is often used.

The present invention will be described in more detail by way of examples, which should not be construed as limiting the scope of the present invention. All % and parts in examples are by weight unless otherwise stated. The weight-average molecular weight is a value determined from gel permeation chromatography using polystyrene as a reference standard.

MONOMER SYNTHESIS EXAMPLE 1
(Synthesis of 2-ethyl-2-adamantyl methacrylate)

50 g of diethyl ether was added to 31.1 g of 2-adamantanone to form a solution. Then, 200 ml of a diethyl ether solution containing ethyl lithium in a concentration of 1.14 mole/liter was added dropwise thereto at such a rate as to keep the temperature of the solution not exceeding 10° C. After stirring the solution at 0° C. for 2 hours as it was, 26.2 g of methacrylic acid chloride (1.2 mole times with respect to 2-methyl-2-adamantanol) was added dropwise thereto at such a rate as to keep the temperature of the solution not exceeding 10° C. After the completion of addition, the solution was stirred at room temperature for 12 hours. Thereafter, deposited inorganic salts were removed by filtration. The organic layer was washed with a 5% by weight aqueous solution of sodium bicarbonate and then washed twice with water. The organic layer was concentrated and distilled under reduced pressure to give 2-ethyl-2-adamantyl methacrylate represented by the following formula.

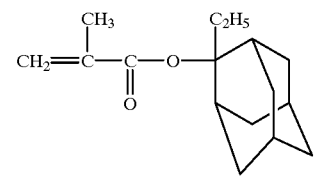

MONOMER SYNTHESIS EXAMPLE 2
(Synthesis of α-methacryloyloxy-γ-butyrolactone)

100 g of α-bromo-γ-butyrolactone and 104.4 g of methacrylic acid (2.0 mole times with respect to α-bromo-γ-butyrolactone) were charged, and methyl isobutyl ketone was added thereto in an amount of three times the weight of α-bromo-γ-butyrolactone to form a solution. To this, 183.6 g of triethylamine (3.0 mole times with respect to α-bromo-γ-butyrolactone) was added dropwise, followed by stirring at room temperature for about 10 hours. After filtration, an organic layer was washed with a 5% by weight aqueous solution of sodium bicarbonate and then washed twice with water. The organic layer was concentrated to give α-methacryloyloxy-γ-butyrolactone represented by the following formula.

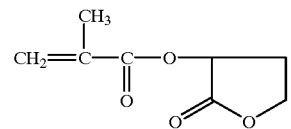

RESIN SYNTHESIS EXAMPLE
(Synthesis of Resin A)

2-Ethyl-2-adamantyl methacrylate, 3-hydroxy-1-adamantyl methacrylate and α-methacryloyloxy-γ-butyrolactone ware charged in a molar ratio of 5:2.5:2.5 (20.0 g: 9.5 g: 7.3 g). Then, methyl isobutyl ketone was added in two times by the weight of the total weight of monomers to form a solution. As an initiator, azobisisobutyronitrile was added in 2 mol % based on the total amount of monomers, followed by heating at 80° C. for about 8 hours. Thereafter, the operation of pouring the reaction solution into a large amount of heptane to cause precipitation was repeated 3 times, whereby purifying the product. As the result, a copolymer having repeating units represented by the following formula and having a weight average molecular weight of about 9,200 was obtained. The copolymer was referred to as resin A.

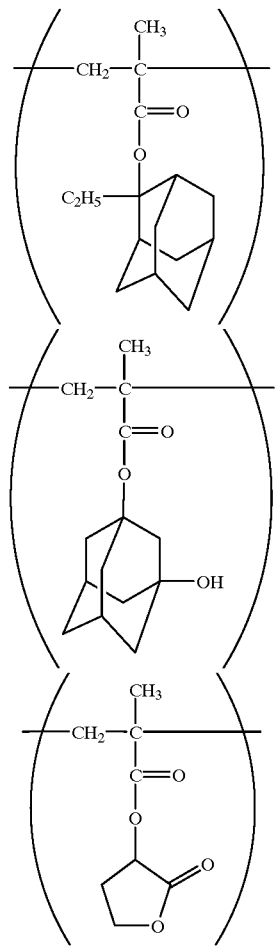

SYNTHESIS EXAMPLE 1 FOR ACID GENERATOR

Synthesis of 1,1'-(2-oxo-1,3-propanediyl)bis(tetrahydrothiophenium) bis(perfluorobutanesulfonate)

(1) Into a four-necked flask were charged 4.7 parts of tetrahydrothiophene, 5.2 parts of dibromoacetone and 47.1 parts of acetone, and they were stirred at room temperature for 24 hours. The deposited crystals were filtered and washed with acetone. The obtained filter cake was combined with ether and the mixture was stirred. After filtration, the filter cake was washed with ether and dried to give 6.4 parts of 1,1'-(2-oxo-1,3-propanediyl)bis(tetrahydrothiophenium) dibromide. Yield: 66.9%.

(2) Into a four-necked flask were charged 1.5 part of 1,1'-(2-oxo-1,-3-propanediyl)bis(tetrahydrothiophenium) dibromide obtained in (1) and 30 parts of acetonitrile. While stirring at room temperature, 2.6 parts of potassium perfluorobutanesulfonate was additionally charged. After stirring at room temperature for 24 hours, the mixture was filtered to remove inorganic salts and the filtrate was concentrated. Thereto, butyl acetate was charged and the mixture was stirred. After filtration, the filter cake was washed with ether and dried to give 1.8 part of the desired product. Yield: 57.2%.

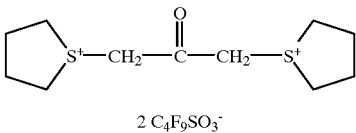

$^1$H-NMR (DMSO-d6, internal standard: tetramethylsilane), δ (ppm): 2.17–2.23 (m, 8H), 3.46–3.59 (m, 8H), 4.67 (s, 4H)

SYNTHESIS EXAMPLE 2 FOR ACID GENERATOR

Synthesis of 4-methyldiphenylsulfonium perfluorooctanesulfonate

Into a four-necked flask were charged 8.0 parts of diphenylsulfoxide and 80.0 parts of toluene, and the mixture was cooled to 2° C. Then, 16.6 parts of trifluoroacetic anhydride and 19.8 parts of perfluorooctanesulfonic acid were charged and the mixture was stirred at the same temperature for 30 minutes. After standing, a lower layer was concentrated and diluted with 340 parts of chloroform. The obtained chloroform solution was washed 6 times with 85 parts of ion-exchange water and concentrated to give 27.7parts of the4-methyldiphenylsulfonium perfluorooctanesulfonate.
:0068

SYNTHESIS EXAMPLE 3 FOR ACID GENERATOR

Synthesis of (2-oxo-1,3-propanediyl)bis(dibutylsulfonium) bis(trifluoromethanesulfonate)

Into a four-necked flask were charged 5.4 parts of dibutyl sulfide, 5.2 parts of dibromoacetone and 54.5 parts of acetonitrile. After stirring at room temperature for 2 hours, 8.8 parts of silver trifluoromethanesulfonate was charged. After stirring at room temperature for 24 hours, the mixture was filtered to remove inorganic salts and the filtrate was concentrated. Thereto, butyl acetate was charged and the mixture was stirred. After filtration, the filter cake was washed with ether and dried to give 5.5 parts of the desired product. Yield: 49.9%.

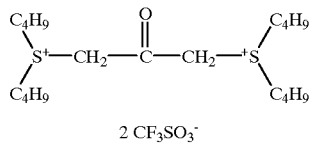

$^1$H-NMR (CDCl$_3$, internal standard: tetramethylsilane), δ (ppm): 0.97–1.02 (t, 12H), 1.46–1.60 (m, 8H), 1.75–1.86 (m, 8H), 3.28–3.51 (m, 8H), 5.06 (s, 4H)

SYNTHESIS EXAMPLE 4 FOR ACID GENERATOR

Synthesis of 2-oxo-1,3-propanediyl)bis(dibutylsulfonium) bis(perfluorobutanesulfonate)

Into a four-necked flask were charged 4.4 parts of dibutyl sulfide, 4.3 parts of dibromoacetone and 44.4 parts of acetonitrile. After stirring at room temperature for 2 hours, 11.3 parts of silver perfluorobutanesulfonate was charged. After stirring at room temperature for 24 hours, the mixture was filtered to remove inorganic salts and the filtrate was concentrated. Thereto, butyl acetate was charged and the mixture was stirred. After filtration, the filter cake was washed with ether and dried to give 2.6 parts of the desired product. Yield: 17.7%.

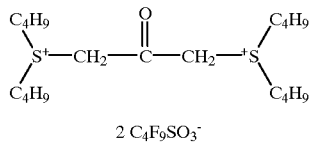

2 C$_4$F$_9$SO$_3^-$ $^1$H-NMR (CDCl$_3$, internal standard: tetramethylsilane), δ (ppm): 0.97–1.02 (t, 12H), 1.46–1.60 (m, 8H), 1.74–1.86 (m, 8H), 3.24–3.48 (m, 8H), 5.09 (s, 4H)

SYNTHESIS EXAMPLE 5 FOR ACID GENERATOR

Synthesis of (2-oxo-1,3-propanediyl)bis(dibutylsulfonium) bis(perfluorooctanesulfonate)

Into a four-necked flask were charged 3.7 parts of dibutyl sulfide, 3.6 parts of dibromoacetone and 37.3 parts of acetonitrile. After stirring at room temperature for 2 hours, 14.2 parts of silver perfluorooctanesulfonate was charged. After stirring at room temperature for 24 hours, the mixture was filtered to remove inorganic salts and the filtrate was concentrated. Thereto, butyl acetate was charged and the mixture was stirred. After filtration, the filter cake was washed with ether and dried to give 3.0 parts of the desired product. Yield: 17.2%.

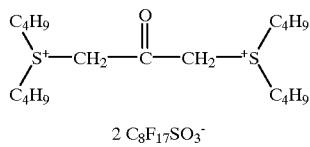

2 C$_8$F$_{17}$SO$_3^-$ $^1$H-NMR (CDCl$_3$, internal standard: tetramethylsilane), δ (ppm): 0.96–1.01 (t, 12H), 1.45–1.58 (m, 8H), 1.73–1.85 (m, 8H), 3.25–3.48 (m, 8H), 5.08 (s, 4H)

Examples, described below, show preparation of resist compositions with acid generators B to F, shown below, and evaluation.

Acid Generator B:
1,1'-(2-oxo-1,3-propanediyl)bis(tetrahydrothiophenium) bis(perfluorobutanesulfonate) (the product in Synthesis Example 1 for Acid Generator)

Acid Generator C:
4-methyldiphenylsulfonium perfluorooctanesulfonate (the product in Synthesis Example 2 for Acid Generator)

Acid Generator D:
(2-oxo-1,3-propanediyl)bis(dibutylsulfonium) bis(trifluoromethanesulfonate) (the product in Synthesis Example 3 for Acid Generator)

Acid Generator E:
(2-oxo-1,3-propanediyl)bis(dibutylsulfonium) bis(perfluorobutanesulfonate) (the product in Synthesis Example 4 for Acid Generator)

Acid Generator F:
(2-oxo-1,3-propanediyl)bis(dibutylsulfonium) bis(perfluorooctanesulfonate) (the product in Synthesis Example 5 for Acid Generator)

EXAMPLE 1

Components listed below were mixed and dissolved. The resultant solution was filtered through a fluorine resin filter having a pore diameter of 0.2 μm to give a resist solution.

| | |
|---|---|
| Resin A | 10 parts |
| Acid generator B | 0.25 part |
| Acid generator C | 0.2 part |
| Quencher: 2,6-diisopropylaniline | 0.02 part |
| 2,6-litidine | 0.01 part |
| Solvent: propyleneglycol monomethylether acetate | 60.8 parts |
| γ-butyrolactone | 3.2 parts |

On a silicon wafer, a composition "DUV-30J-14" manufactured by Brewer Co. Ltd. was applied and baked under conditions of 215° C. for 60 seconds so that an organic anti-reflective layer having a thickness of 1,600 angstrom was formed on the wafer. The resist solution obtained above was applied by spin-coating on said wafer so that the film thickness after drying was 0.335 μm. After applying the resist solution, the wafer was pre-baked on a direct hotplate at 120° C. for 60 seconds.

The wafer having a resist film formed thereon was irradiated with an ArF eximer stepper ["NSR-ArF", manufactured by Nikon, NA=0.55, σ=0.6] through a line-and-space pattern, changing stepwise the exposure amount. The exposed wafer was subjected to post-exposure baking (PEB) on a hot plate at 150° C. for 60 seconds. Then the wafer was subjected to paddle development with 2.38% by weight aqueous tetramethyl ammonium hydroxide solution for 60 seconds. The developed pattern was observed by a scanning electron microscope and assessed for the effective sensitivity and the resolution by the following methods. The effective sensitivity was 88 mJ/cm$^2$, and the resolution was 0.13 μm.

Effective sensitivity: This is expressed in the minimum amount of exposure which gave 1:1 line-and-space pattern of 0.18 μm.

Resolution: This is expressed in the minimum size which gave line-and-space pattern spitted at the exposure amount of the effective sensitivity.

Cross sectional photograph by a scanning electron microscope of Line-and-space pattern of 0.18 μm at exposure amount of the effective sensitivity was observed. It was observed that sides of the pattern were vertical and the top surfaces of the pattern were almost flat.

The above resist solutions were applied on quartz glass wafers to form resist films having a film thickness after prebake of 0.355 μm. The transmittance of resist films at 193 nm was measured with a spectrophotometer. As the result, a transmittance of 67% was obtained. As described above, these resists showed a high transmittance and had a good resolution.

EXAMPLES 2–4 AND COMPARATIVE EXAMPLE 1

Components listed below were mixed and dissolved. The resultant solution was filtered through a fluorine resin filter having a pore diameter of 0.2 μm to give a resist solution.

| | |
|---|---|
| Resin A | 10 parts |
| Acid generator (1) shown in Table 1 | 0.5 part |
| Acid generator C | 0.2 part |
| Quencher: 2, 6-diisopropylaniline | 0.015 part |
| Solvent: propyleneglycol monomethylether acetate | 60.8 parts |
| γ-butyrolactone | 3.2 parts |

On a silicon wafer, a composition "DUV-30J-14" manufactured by Brewer Co. Ltd. was applied and baked under conditions of 215° C. for 60 seconds so that an organic anti-reflective layer having a thickness of 1,600 angstrom was formed on the wafer. The resist solution obtained above was applied by spin-coating on said wafer so that the film thickness after drying was 0.335 μm. After applying the resist solution, the wafer was pre-baked on a direct hotplate at 110° C. for 60 seconds.

The wafer having a resist film formed thereon was irradiated with an ArF eximer stepper ["NSR-ArF", manufactured by Nikon, NA=0.55, σ=0.6] through a line-and-space pattern, changing stepwise the exposure amount. The exposed wafer was subjected to post-exposure baking (PEB) on a hot plate at 150° C. for 60 seconds. Then the wafer was subjected to paddle development with 2.38% by weight aqueous tetramethyl ammonium hydroxide solution for 60 seconds. The developed pattern was observed by a scanning electron microscope and assessed for the effective sensitivity and the resolution by the methods above. The results are shown in Table 1.

The above resist solutions were applied on quartz glass wafers to form resist films having a film thickness after prebake of 0.355 μm. The transmittance of resist films at 193 nm was measured with a spectrophotometer. This result is also shown in Table 1.

TABLE 1

| Example No. | Acid generator (1) | Effective sensitivity (mJ/cm$^2$) | Resolution (μm) | Transmittance (%) |
|---|---|---|---|---|
| Example 2 | D | 51 | 0.16 | 71 |
| Example 3 | E | 57 | 0.15 | 67 |
| Example 4 | F | 69 | 0.15 | 67 |
| Comparative Example 1 | none | 59 | 0.17 | 71 |

The chemical amplification type positive resist composition of the invention, which contains specific acid generators, has high transmittance, is superior in sensitivity and resolution in a lithography utilizing a light having a wavelength of 220 nm or lower, for example, ArF eximer laser light, and confers a good profile.

What is claimed is:

1. A chemical amplifying type positive resist composition comprising an aliphatic sulfonium salt represented by the following formula (I):

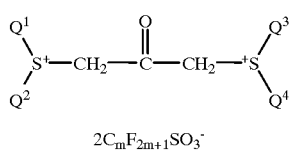

(I)

wherein either $Q^1$, $Q^2$, $Q^3$ and $Q^4$ independently represent an alkyl group having 1 to 6 carbon atoms or a cycloalkyl group having 3 to 10 carbon atoms, or $Q^1$ and $Q^2$ and/or $Q^3$ and $Q^4$ independently form, together with the adjacent sulfur atom, a heterocyclic group which has 2 to 8 carbon atoms and which may further have an oxygen atom or a sulfur atom, and m represents an integer of 1 to 8;

at least one onium salt selected from the group consisting of a triphenylsulfonium salt represented by the following formula (IIa) and a diphenyliodonium salt represented by the following formula (IIb):

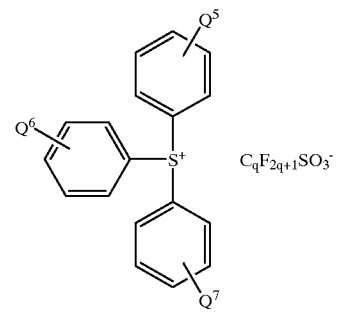

(IIa)

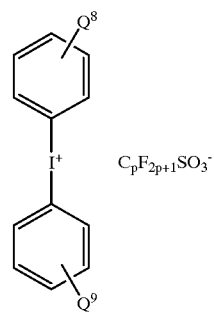

(IIb)

wherein $Q^5$, $Q^6$, $Q^7$, $Q^8$ and $Q^9$ independently represent a hydrogen atom, a hydroxyl group, an alkyl group having 1 to 6 carbon atoms or an alkoxy group having 1 to 6 carbon atoms, and p and q represent integer of 1 to 8; and a resin which contains a polymerization unit having a group unstable to an acid, and which is insoluble in alkali by itself but becomes soluble in alkali by the action of an acid.

2. The chemical amplifying type positive resist composition according to claim 1 wherein the ratio by weight of the aliphatic sulfonium salt of the formula (I) to the onium salt selected from the group consisting of a triphenylsulfonium salt of the formula (IIa) and a diphenyliodonium salt of the formula (IIb) is about 9:1 to 1:9.

3. The chemical amplifying type positive resist composition according to claim 1 wherein the resin contains the polymerization unit having a group unstable to an acid in a range of 10 to 80% by mole based on the total resin.

4. The chemical amplifying type positive resist composition according to claim 1 wherein the polymerization unit having a group unstable to an acid is a polymerization unit of 2-alkyl-2-adamantyl (meth)acrylate.

5. The chemical amplifying type positive resist composition according to claim 1 wherein the resin further contain a polymerization unit selected from polymerization units of 3-hydroxy-1-adamantyl (meth)acrylate and polymerization units of (meth)acryloyloxy-γ-butyrolactone in which the lactone ring is unsubstituted or substituted with an alkyl.

6. The chemical amplifying type positive resist composition according to claim 5 wherein the resin is a terpolymer containing a polymerization unit having a group unstable to an acid, a polymerization unit of 3-hydroxy-1-adamantyl (meth)acrylate and a polymerization unit of (meth)acryloyloxy-γ-butyrolactone in which the lactone ring is unsubstituted or substituted with an alkyl.

7. The chemical amplifying type positive resist composition according to claim 5 wherein the polymerization unit of (meth)acryloyloxy-γ-butyrolactone in which the lactone ring is unsubstituted or substituted with an alkyl is a polymerization unit of α-(meth)acryloyloxy-γ-butyrolactone which is unsubstituted or alkyl-substituted in the lactone ring, or a polymerization unit of β-(meth)acryloyloxy-γ-butyrolactone which is unsubstituted or alkyl-substituted in the lactone ring.

8. The chemical amplifying type positive resist composition according to claim 1 wherein the resin further contains a polymerization unit of aliphatic unsaturated dicarboxylic anhydride and a polymerization unit of 2-norbornene.

9. The chemical amplifying type positive resist composition according to claim 8 wherein the resin is a polymer containing a polymerization unit of aliphatic unsaturated dicarboxylic anhydride and a polymerization unit of 2-norbornene as well as a polymerization unit selected from a polymerization units of 3-hydroxy-1-adamantyl (meth)acrylate and polymerization units of (meth)acryloyloxy-γ-butyrolactone in which the lactone ring is unsubstituted or substituted with an alkyl.

10. The chemical amplifying type positive resist composition according to claim 1 which further comprises a basic compound as a quencher.

11. The chemical amplifying type positive resist composition according to claim 10 wherein the basic compound is 2,6-dialkylpyridine compound represented by the formula (X):

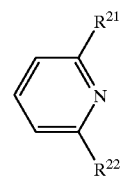

(X)

wherein $R^{21}$ and $R^{22}$ independently represent an alkyl having 1–4 carbon atoms.

12. An aliphatic sulfonium salt represented by the following formula (I):

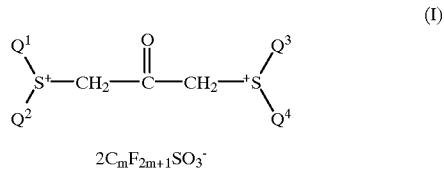

(I)

wherein either $Q^1$, $Q^2$, $Q^3$ and $Q^4$ independently represent an alkyl group having 1 to 6 carbon atoms or a cycloalkyl group having 3 to 10 carbon atoms, or $Q^1$ and $Q^2$ and/or $Q^3$ and $Q^4$ independently form, together with the adjacent sulfur atom, a heterocyclic group which has 2 to 8 carbon atoms and which may further have an oxygen atom or a sulfur atom, and m represents an integer of 1 to 8.

* * * * *